US011131568B2

(12) United States Patent
Jo et al.

(10) Patent No.: US 11,131,568 B2
(45) Date of Patent: Sep. 28, 2021

(54) SENSOR PACKAGE, METHOD OF MANUFACTURING THE SAME, AND METHOD OF MANUFACTURING LID STRUCTURE

(71) Applicant: Samsung Electronics Co., Ltd., Suwon-si (KR)

(72) Inventors: Sungeun Jo, Incheon (KR); Youngshin Kwon, Suwon-si (KR); Minjin Kim, Seoul (KR); Woonbae Kim, Seoul (KR); Youngdoo Jung, Suwon-si (KR); Eunhee Jung, Hwaseong-si (KR); Inho Choi, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 17/002,071

(22) Filed: Aug. 25, 2020

(65) Prior Publication Data

US 2020/0386585 A1    Dec. 10, 2020

Related U.S. Application Data

(63) Continuation of application No. 16/131,467, filed on Sep. 14, 2018, now Pat. No. 10,760,930.

(30) Foreign Application Priority Data

Dec. 20, 2017  (KR) .......................... 10-2017-0175809

(51) Int. Cl.
  *G01D 11/24*    (2006.01)
  *G01N 33/00*    (2006.01)

(52) U.S. Cl.
  CPC ....... *G01D 11/245* (2013.01); *G01N 33/0009* (2013.01)

(58) Field of Classification Search
  CPC .................... G01D 11/245; G01N 33/0009
  See application file for complete search history.

(56) References Cited

U.S. PATENT DOCUMENTS 5,798,556 A * 8/1998 Hughes .................. G01N 27/12
                                                          257/414
7,360,395 B2 * 4/2008 Sasaki .................. G01N 33/006
                                                           73/25.03
(Continued)

FOREIGN PATENT DOCUMENTS

JP    2008139165 A    6/2008
JP    4610776 B2      1/2011
(Continued)

*Primary Examiner* — Jamel E Williams
(74) *Attorney, Agent, or Firm* — Muir Patent Law, PLLC

(57) ABSTRACT

Disclosed are sensor packages, methods of manufacturing the same, and methods of manufacturing lid structures. The sensor package comprises a package substrate, a gas sensor on the package substrate, a lid on the package substrate and having a hole extending between a first inner surface and a first outer surface of the lid, the first inner surface of the lid facing toward the package substrate and the first outer surface of the lid facing away from the package substrate, and a waterproof film in the hole of the lid. The waterproof film is formed on the first inner surface and the first outer surface of the lid.

20 Claims, 19 Drawing Sheets

(56) References Cited

U.S. PATENT DOCUMENTS

| | | | |
|---|---|---|---|
| 7,418,855 B2* | 9/2008 | Oishi | G01N 33/0011 73/25.03 |
| 7,479,255 B2 | 1/2009 | Otani et al. | |
| 7,827,847 B2* | 11/2010 | Oishi | G01N 27/16 73/23.2 |
| 8,486,218 B2 | 7/2013 | Asuke | |
| 8,815,161 B2* | 8/2014 | Oishi | G01N 33/005 422/94 |
| 9,156,684 B1 | 10/2015 | Minervini | |
| 9,746,390 B2 | 8/2017 | Schoot Uiterkamp et al. | |
| 9,783,412 B2 | 10/2017 | Guan et al. | |
| 9,790,089 B2 | 10/2017 | Dawson et al. | |
| 9,878,900 B2 | 1/2018 | Wu | |
| 2004/0093930 A1* | 5/2004 | Matsunami | G01N 33/0009 73/31.07 |
| 2005/0042141 A1* | 2/2005 | Otani | G01N 27/16 422/98 |
| 2016/0178565 A1 | 6/2016 | Chapples et al. | |
| 2016/0282212 A1 | 9/2016 | Beer et al. | |
| 2017/0059320 A1 | 3/2017 | Sugimoto et al. | |
| 2017/0081179 A1 | 3/2017 | Dawson et al. | |
| 2017/0101307 A1 | 4/2017 | Lim et al. | |
| 2017/0131230 A1 | 5/2017 | Papageorge et al. | |
| 2017/0142524 A1 | 5/2017 | Sooriakumar et al. | |
| 2017/0292863 A1 | 10/2017 | Umetsu | |
| 2019/0204281 A1* | 7/2019 | Choi | G01N 33/006 |
| 2019/0212312 A1* | 7/2019 | Kim | H01L 23/02 |
| 2019/0232231 A1* | 8/2019 | Lin | G01N 33/0009 |

FOREIGN PATENT DOCUMENTS

| | | |
|---|---|---|
| JP | 2011-150513 A | 8/2011 |
| JP | 4892521 B2 | 3/2012 |
| KR | 10-1469606 B1 | 12/2014 |

* cited by examiner

SENSOR PACKAGE, METHOD OF MANUFACTURING THE SAME, AND METHOD OF MANUFACTURING LID STRUCTURE

CROSS-REFERENCE TO RELATED APPLICATIONS

This U.S. nonprovisional application is a continuation of and claims priority to U.S. patent application Ser. No. 16/131,467 filed on Sep. 14, 2018, which claims priority under 35 U.S.C § 119 to Korean Patent Application No. 10-2017-0175809 filed on Dec. 20, 2017, in the Korean Intellectual Property Office, the entire contents of each of which are hereby incorporated by reference.

BACKGROUND

Example embodiments according to inventive concepts relate to a sensor package, and more particularly, to a sensor package provided with a waterproof film.

A gas sensor measures the amount of an analysis target gas by using characteristics of changes in electrical conductivity or electrical resistance in accordance with adsorption of molecules of the analysis target gas. The gas sensor may be manufactured using metal oxide semiconductor, solid electrolyte material, or other organic materials. The gas sensor may be required to have improved accuracy with importance of recent environmental issues and development of industry.

SUMMARY

Some embodiments of inventive concepts provide a sensor package having improved sensing accuracy and a method of manufacturing the same.

According to exemplary embodiments of inventive concepts, a sensor package may comprise: a package substrate; a gas sensor on the package substrate; a lid on the package substrate and positioned over the gas sensor, the lid having a hole extending between a first inner surface and a first outer surface of the lid, the first inner surface of the lid facing toward the package substrate and the first outer surface of the lid facing away from the package substrate; and a waterproof film in the hole of the lid, wherein the waterproof film is formed on the first inner surface and the first outer surface of the lid.

According to exemplary embodiments of inventive concepts, a method of manufacturing a sensor package may comprise: preparing a lid structure; and placing the lid structure on a package substrate. The lid structure may comprise: a lid having a hole extending between an inner surface and an outer surface of the lid, the inner surface of the lid facing toward the package substrate and the outer surface of the lid facing away from the package substrate; and a waterproof film in the hole and formed on the inner surface and the outer surface of the lid.

According to exemplary embodiments of inventive concepts, a method of manufacturing a lid structure may comprise: preparing a lid having a hole extending between an inner surface and an outer surface of the lid; filling the hole with a waterproof solution by placing a portion of the lid into the waterproof solution; and curing the waterproof solution to form a waterproof film in the hole.

BRIEF DESCRIPTION OF THE DRAWINGS

Example embodiments will be more clearly understood from the following detailed description taken in conjunction with the accompanying drawings. FIGS. 1 to 6 represent non-limiting, example embodiments as described herein.

FIG. 1 illustrates a plan view showing a sensor package according to exemplary embodiments.

FIG. 6 illustrates a plan view showing a sensor package according to exemplary embodiments.

DETAILED DESCRIPTION OF EMBODIMENTS

Figure 1:
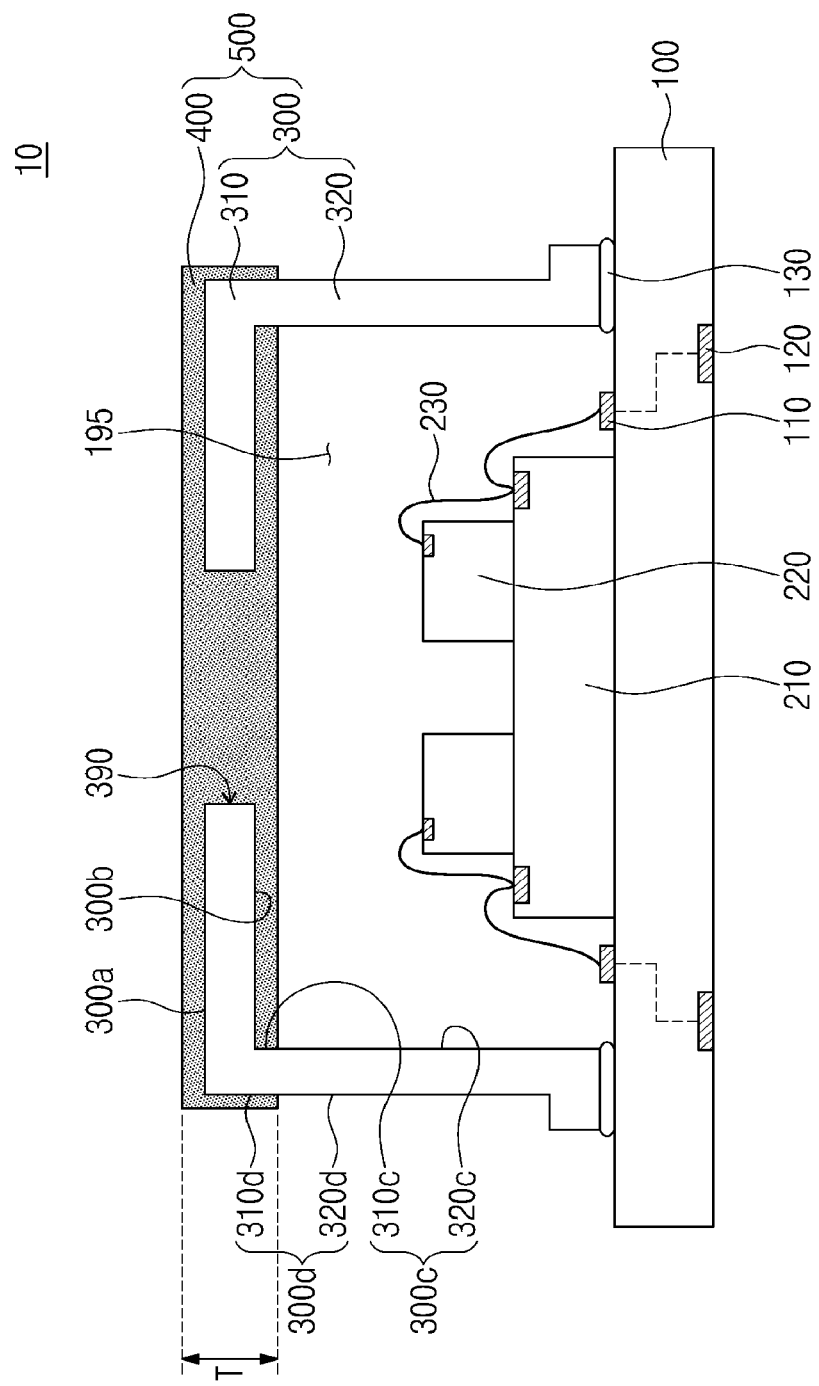

It will be described hereinafter exemplary embodiments of inventive concepts with reference to the accompanying drawings. Like reference numerals may indicate like components throughout the description.

A sensor package and its manufacturing method according to inventive concepts will now be described below.

FIG. 1 illustrates a plan view showing a sensor package according to exemplary embodiments.

Referring to FIG. 1, a sensor package 10 may include a package substrate 100, a sensing device 220, and a lid structure 500. The sensor package 10 may be a gas sensor package for sensing gases. The package substrate 100 may include, for example, a printed circuit board (PCB). An upper conductive pad 110 and a lower conductive pad 120 may be respectively disposed on top and bottom surfaces of the package substrate 100. The upper conductive pad 110 may be electrically connected through an internal wiring line to the lower conductive pad 120. In figures, a dotted line schematically indicates an internal wiring line within the package substrate 100. The lower conductive pad 120 may be coupled to an external device.

A plurality of devices 210 and 220 may be disposed on the package substrate 100. The devices 210 and 220 may include a control device 210 (e.g., control circuitry) and a sensing device 220 (e.g., sensing circuitry). The control device 210 may include a semiconductor chip. The control device 210 may include a plurality of integrated circuits such as complementary metal-oxide-semiconductor (CMOS) transistors. The control device 210 may control the sensing device 220. The control device 210 may be electrically connected through a bonding wire 230 to the upper conductive pad 110. The sensing device 220 may be stacked on a top surface of the control device 210. For example, the sensing device 220 may include a gas sensor chip for sensing gases. The sensing device 220 may have a top surface serving as a sensing face. The sensing device 220 may be electrically connected through the bonding wire 230 to the control device 210. The sensing device 220 may be electrically connected through the control device 210 to the upper conductive pad 110.

According to exemplary embodiments, an electrical connection of the devices 210 and 220 may be achieved in various manners. For example, one or more of the control device 210 and the sensing device 220 may be electrically flip-chip connected to the package substrate 100. In this description, the phrase "electrically connected to the control device 210/sensing device 220" may mean "electrically connected to integrated circuits of the control device 210/sensing device 220." An arrangement of the devices 210 and 220 may be diversely changed. For example, the sensing device 220 and the control device 210 may be laterally spaced apart from each other on the package substrate 100. The sensing device 220 may be provided in plural. In some embodiments, for another example, the control device 210 may not be provided, and instead the sensing device 220 may further serve as the control device 210. The control device 210 and the sensing device 220 will be further discussed below, but inventive concepts are not limited to the following description.

The various pads (110, 120) of a device described herein may be conductive terminals connected to internal wiring of the device, and may transmit signals and/or supply voltages between an internal wiring and/or internal circuit of the device and an external source. For example, chip pads of a semiconductor chip may electrically connect to and transmit supply voltages and/or signals between an integrated circuit of the semiconductor chip and a device to which the semiconductor chip is connected. The various pads may be provided on or near an external surface of the device and may generally have a planar surface area (often larger than a corresponding surface area of the internal wiring to which they are connected) to promote connection to a further terminal, such as a bump or solder ball, and/or an external wiring.

The lid structure 500 may be disposed on the package substrate 100. The lid structure 500 may include a lid 300 and a waterproof film 400. The term "waterproof film" as used herein may refer to a film that may allow a gas to pass through, but not allow impurities to pass through. The package substrate 100 and the lid 300 may define a cavity 195 therebetween. For example, the cavity 195 may be a space surrounded by the package substrate 100 and the lid 300. The cavity 195 may be occupied by a gas. The gas may include an analysis target material. The lid 300 may include a metal, a plastic, or a liquid-crystal polymer. The lid 300 may protect the devices 210 and 220 from external stresses. The external stresses may be or include, for example, physical impact or impurities. The impurities may include moisture and/or dust.

The lid 300 may include a first portion 310 and a second portion 320. The second portion 320 of the lid 300 may be provided between the first portion 310 and the package substrate 100. The second portion 320 of the lid 300 may support the first portion 310. The upper portion of the second portion 320 of the lid 300 may be connected to the first portion 310 and the lower portion of the second portion 320 may be connected to the upper surface of the package substrate 100. In some embodiments, the first portion 310 and the second portion 320 may be integrally formed as a single unit to form the lid 300. The first portion 310 may extend inward parallel to the upper surface of the package substrate 100 and the second portion 320 may extend vertically from the upper surface of the package substrate 100 to be connected to the first portion 310 thereby forming an upside down L-shaped lid 300.

For example, the lid 300 may have a first inner surface 300b, a first outer surface 300a, a second inner surface 300c, and a second outer surface 300d. The first inner surface 300b of the lid 300 may stand facing toward the package substrate 100. The first outer surface 300a may be opposite to the first inner surface 300b facing away from the package substrate 100. The first outer surface 300a of the lid 300 may correspond to an uppermost surface of the lid 300. The second outer surface 300d of the lid 300 may correspond to an outer sidewall of the lid 300. For example, the lid 300 may have an edge provided at a location the first outer surface 300a meets the second outer surface 300d. The second outer surface 300d of the lid 300 may include a first sub-outer surface 310d and a second sub-outer surface 320d. The first sub-outer surface 310d may correspond to an outer sidewall of the first portion 310, and the second sub-outer surface 320d may correspond to an outer sidewall of the second portion 320. The second sub-outer surface 320d may be closer than the first sub-outer surface 310d to the package substrate 100. For example, the first sub-outer surface 310d may correspond to an outer sidewall of an upper portion (e.g., the first portion 310) of lid 300, and the second sub-outer surface 320d may correspond to an outer sidewall of a lower portion (e.g., the second portion 320) of the lid 300 that connects the uppermost surface of the lid 300 to the package substrate 100. The second sub-outer surface 320d may be connected to the first sub-outer surface 310d. The second inner surface 300c of the lid 300 may face the second outer surface 300d. The second inner surface 300c of the lid 300 may correspond to an inner sidewall of the lid 300. The second inner surface 300c of the lid 300 may include a first sub-inner surface 310c and a second sub-inner surface 320c. The first sub-inner surface 310c may face the first sub-outer surface 310d. The first sub-inner surface 310c may correspond to the outer sidewall of the first portion 310. The second sub-inner surface 320c may be connected to the first sub-inner surface 310c. The second sub-inner surface 320c may face the second sub-outer surface 320d. The second sub-inner surface 320c may correspond to the outer sidewall of the second portion 320.

The lid 300 may include at least one hole 390. The hole 390 may penetrate the first inner surface 300b and the first outer surface 300a. Differently from that shown, the hole 390 may be provided in plural.

The waterproof film 400 may be provided in the hole 390. The waterproof film 400 may fill, for example, the hole 390. The waterproof film 400 may cover the first portion 310 of the lid 300. For example, the waterproof film 400 may extend onto the first outer surface 300a, the first inner surface 300b, and the first sub-inner surface 310c of the lid 300. The waterproof film 400 may further extend onto the first sub-outer surface 310d. The waterproof film 400 may expose the second portion 320 of the lid 300. For example, the waterproof film 400 may not cover the second sub-inner surface 320c and the second sub-outer surface 320d of the lid 300.

When an external material enters the cavity 195, it may be required that the external material pass through the waterproof film 400 provided in the hole 390. The external material may include a gas and impurities. The impurities may include moisture and/or dust. The gas may include an analysis target material. The waterproof film 400 may allow the gas to pass through and enter the cavity 195. The sensing device 220 may sense the entered gas. The impurities may have difficulty in passing through the waterproof film 400. The occurrence of sensing noise due to the impurities may thus be prevented to improve sensing accuracy of the sensing device 220. It may be possible to prevent or reduce impurity-induced damages to the sensing device 220.

The phrase "passing through the waterproof film 400" may mean "passing through pores (not shown) of the waterproof film 400." When the pores of the waterproof film 400 have a diameter less than about 0.1 μm, the gas may have difficulty in passing through the waterproof film 400. When the pores of the waterproof film 400 have a diameter greater than about 10 μm, the impurities may pass through the waterproof film 400. In some embodiments, the pores of the waterproof film 400 may have a diameter ranging from about 0.1 μm to about 10 μm. The waterproof film 400 may accordingly allow the gas to pass through, but not allow the impurities to pass through.

In some embodiments, a material of the waterproof film 400 may be properly chosen to select substance passing through the waterproof film 400. For example, the waterproof film 400 may include a hydrophobic polymer to prevent the cavity 195 from receiving hydrophilic impurities such as moisture. The hydrophobic polymer may include, for example, poly(tetrafluoroethylene) (hereinafter referred to as "PTFE").

A thickness T of the waterproof film 400 may be appropriately adjusted to select substance passing through the waterproof film 400. The waterproof film 400 may include a portion provided in the hole 390, and a thickness of the portion may correspond to the thickness T of the waterproof film 400. When the thickness T of the waterproof film 400 is less than about 10 μm, the waterproof film 400 may allow the impurities to pass through or may decrease in strength. When the thickness T of the waterproof film 400 is greater than about 500 μm, the gas may have difficulty in passing through the waterproof film 400. In some embodiments, the thickness T of the waterproof film 400 may fall within a range from about 10 μm to about 500 μm. The waterproof film 400 may thus selectively allow the gas to pass through. The waterproof film 400 may be homogenously formed of the same material.

A connection member 130 may be provided between the package substrate 100 and the lid 300. The connection member 130 may include an adhesive or solder. The connection member 130 may seal a gap between the package substrate 100 and the lid 300. As such, no external impurities may be introduced into the cavity 195. Differently from that shown, the connection member 130 may be shaped like a solder ball or bump. The lid 300, together with the package substrate 100 and connection member 130, may encapsulate the devices 210 and 220 and seal the same within cavity 195. With the exception of gas allowed to pass through waterproof film 400, the cavity may be hermetically sealed and thus only allow gas to flow in an out of cavity 195 via pores of the waterproof film 400.

Hereinafter, it will be described methods of manufacturing sensor packages according to exemplary embodiments. In the description of the manufacturing methods, top and bottom surfaces will be defined based on the sensor package of FIG. 1.

Figure 2A:
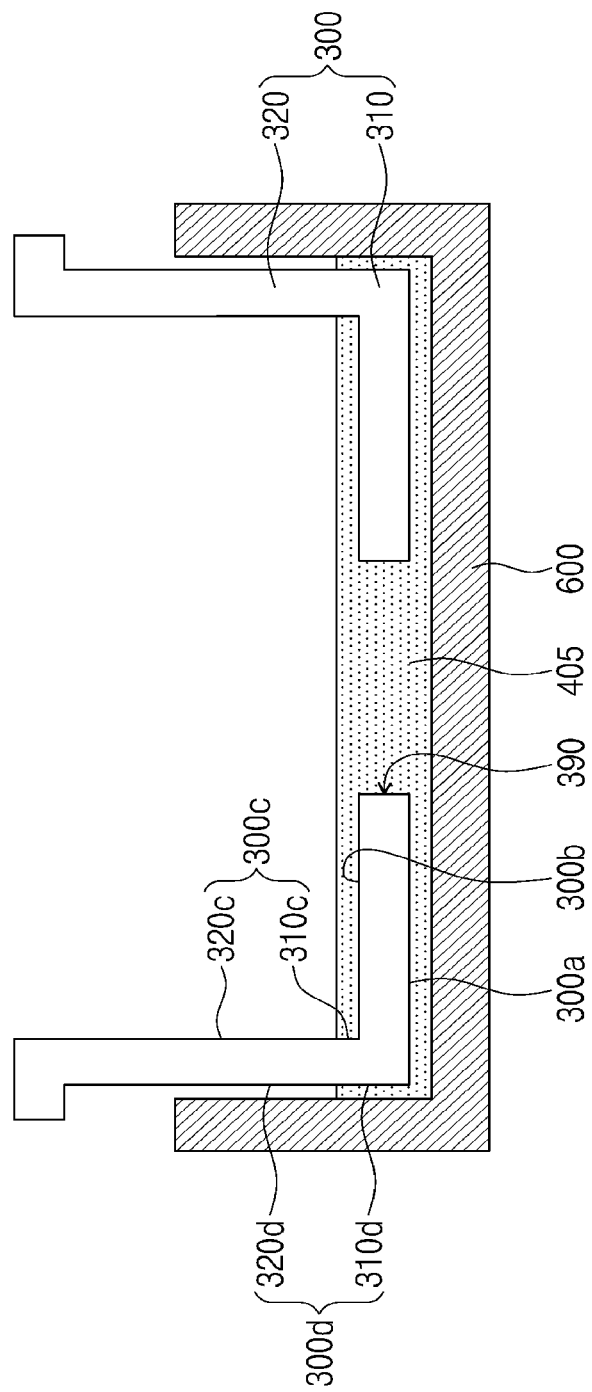
FIGS. 2A to 2C illustrate cross-sectional views showing a method of manufacturing a sensor package according to exemplary embodiments.
Figure 2B:
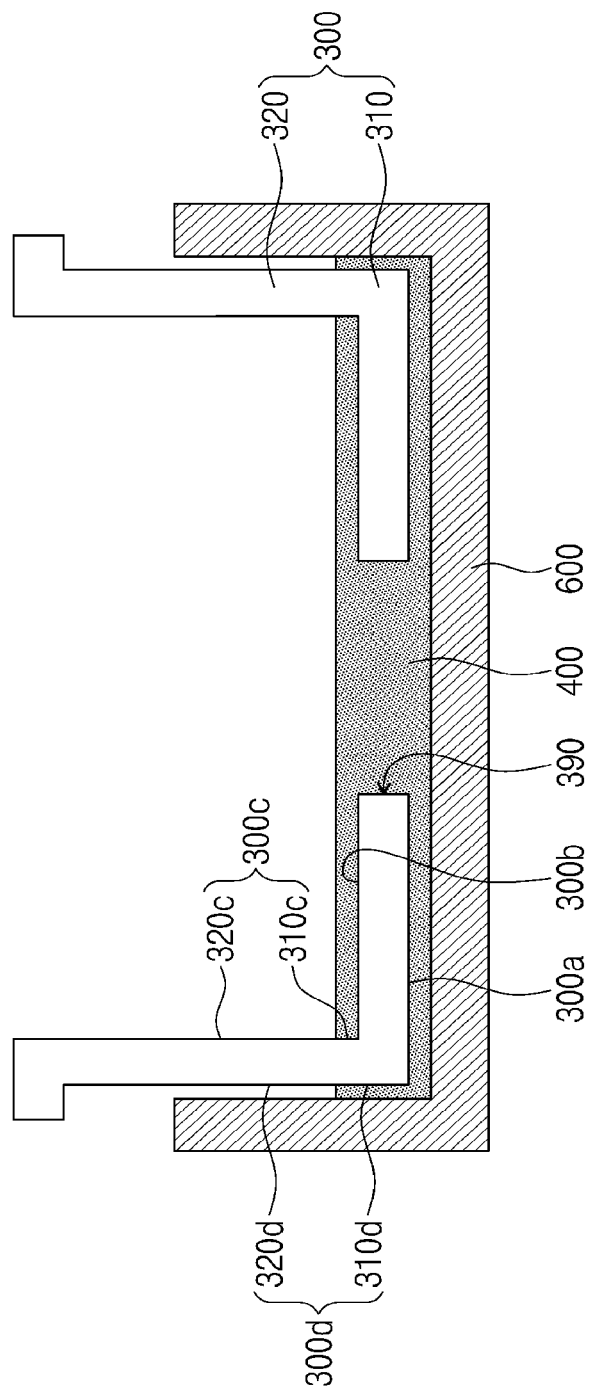
Figure 2C:
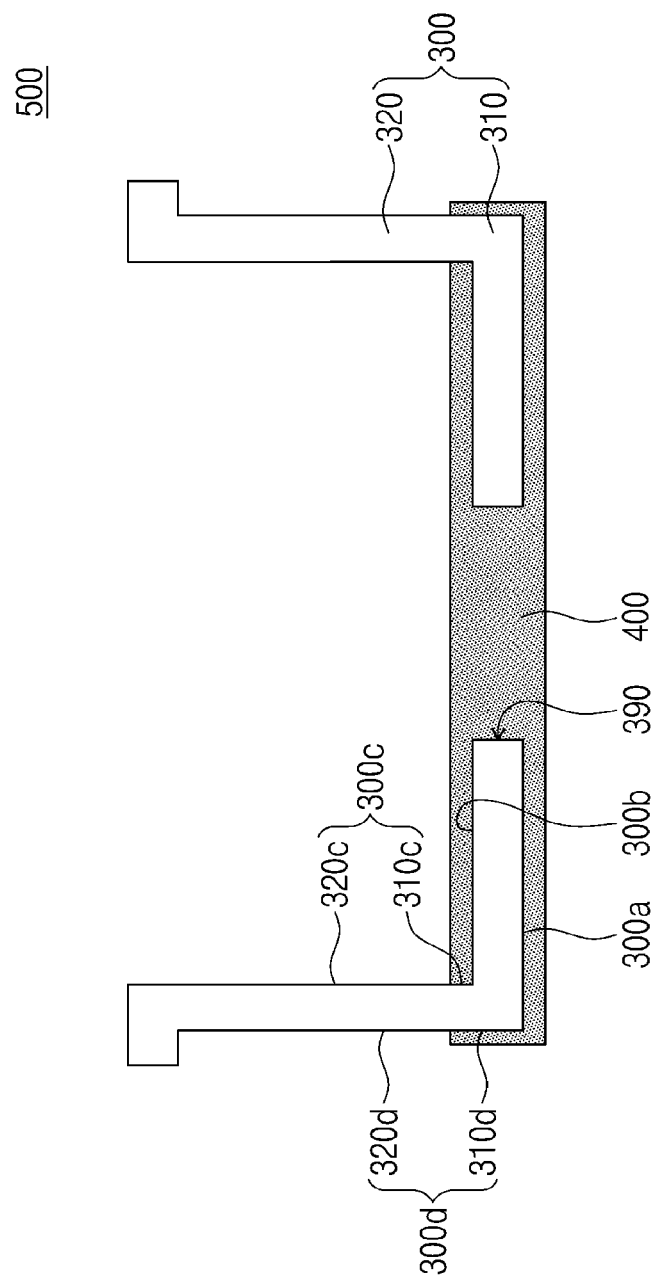

FIGS. 2A to 2C illustrate cross-sectional views showing a method of manufacturing a sensor package according to exemplary embodiments. In the embodiment that follows, a description duplicate with the aforementioned will be omitted.

Referring to FIG. 2A, a lid 300 may be provided in a waterproof solution 405. A container 600 may be provided to accommodate the waterproof solution 405. The waterproof solution 405 may include a hydrophobic polymer such as PTFE. A first portion 310 of the lid 300 may be provided in the waterproof solution 405. The providing of the lid 300 may continue until a first inner surface 300b and a first outer surface 300a of the lid 300 are immersed in the waterproof solution 405. A hole 390 may thus be filled with the waterproof solution 405. A second portion 320 of the lid 300 may not be immersed in the waterproof solution 405.

Referring to FIG. 2B, the waterproof solution 405 of FIG. 2A may be cured to form a waterproof film 400. The curing of the waterproof solution 405 may be performed by thermal curing or optical curing. The waterproof film 400 may be formed in the hole 390 and on the first inner surface 300b, the first outer surface 300a, and a first sub-outer surface 310d of the lid 300. The waterproof film 400 may further extend onto the first sub-outer surface 310d of the lid 300. Since the waterproof solution 405 is cured to form the waterproof film 400, the formation of the waterproof film 400 may have no limitation due to a diameter of the hole 390 and/or the number of the hole 390. The waterproof film 400 may thus be manufactured in a simplified process.

Referring to FIG. 2C, the waterproof film 400 may be separated from the container 600, with the result that a lid structure 500 may be fabricated. The waterproof film 400 may be physically separated from the container 600. The lid structure 500 may include the lid 300 and the waterproof film 400.

Referring back to FIG. 1, devices 210 and 220 may be mounted on a package substrate 100. The lid structure 500 may be disposed on the package substrate 100 in such a way that the first inner surface 300b of the lid 300 may face the package substrate 100 and may extend parallel to the upper surface of the package substrate 100. A connection member 130 may be formed between the package substrate 100 and the lid 300, such that the lid 300 may be fixed on the package substrate 100. Through the aforementioned exemplary processes, a sensor package 10 may be eventually manufactured.

FIGS. 3A to 3D illustrate cross-sectional views showing a method of manufacturing a sensor package according to exemplary embodiments. In the embodiment that follows, a description duplicate with the aforementioned will be omitted.

Figure 3A:
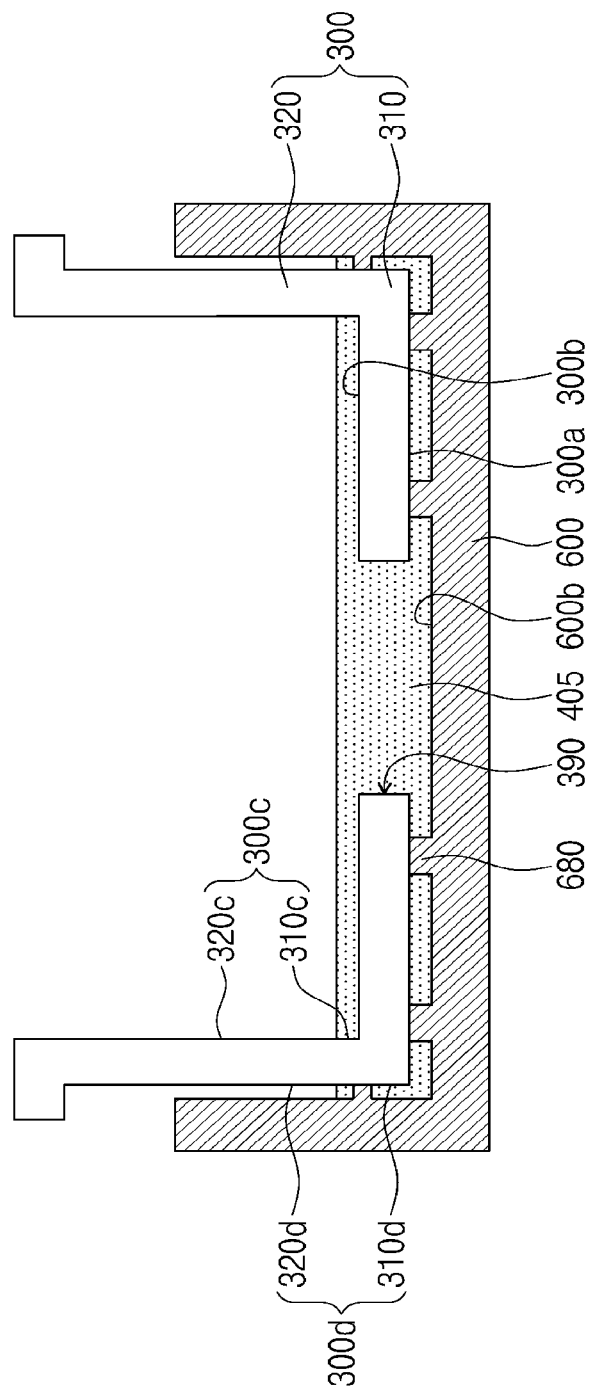
FIGS. 3A to 3D illustrate cross-sectional views showing a method of manufacturing a sensor package according to exemplary embodiments.

Referring to FIG. 3A, a container 600 having protrusions 680 may be prepared. The container 600 may have the protrusions 680 on its inner surface 600b. A waterproof solution 405 may be provided on the inner surface 600b of the container 600. A lid 300 may be provided in the container 600, and thus a first portion 310 of the lid 300 may be immersed in the waterproof solution 405. In this step, the lid 300 may be disposed on and in physical contact with the protrusions 680. The protrusions 680 may cause the lid 300 to be spaced apart at a predetermined interval from the inner surface 600b of the container 600. The waterproof solution 405 may fill a gap between the container 600 and the lid 300. The number and shape of the protrusions 680 may not be limited to that shown, but variously changed.

Figure 3B:
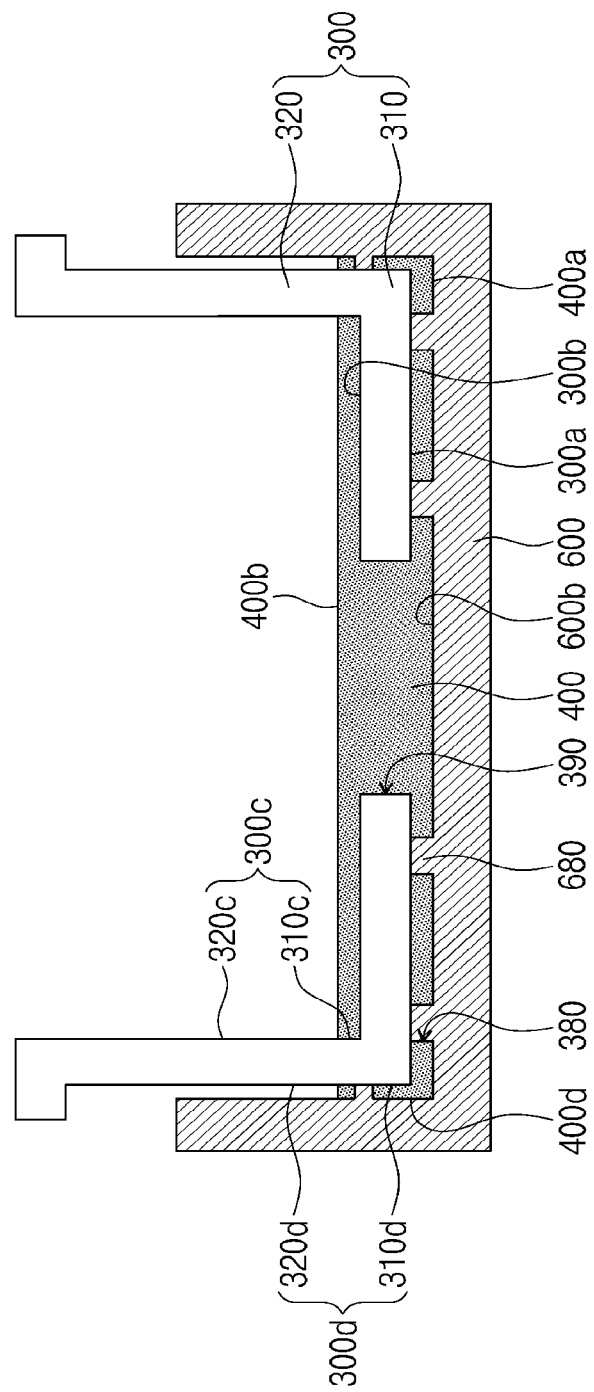

Referring to FIG. 3B, the waterproof solution 405 may be cured to form a waterproof film 400. The waterproof film 400 may have recesses 380. The recesses 380 may be formed by the protrusions 680 of the container 600. The recesses 380 may be provided on a top surface 400a of the waterproof film 400. The recesses 380 may further be formed on an outer surface 400d of the waterproof film 400. In contrast, the recesses 380 may not be formed on a bottom surface 400b of the waterproof film 400. In this exemplary embodiment, the top surface 400a of the waterproof film 400 may face away from the first inner surface 300b of the lid 300 and the first inner surface 300b of the lid 300 may face toward the bottom surface 400b.

Figure 3C:
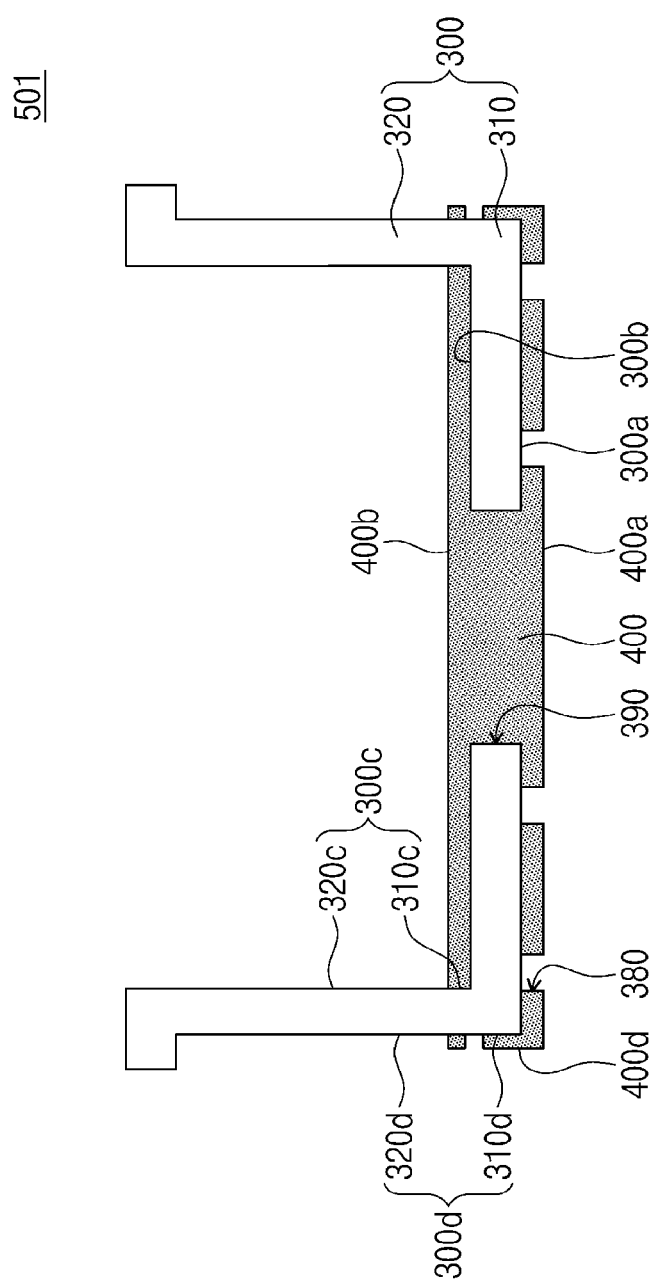
Figure 3D:
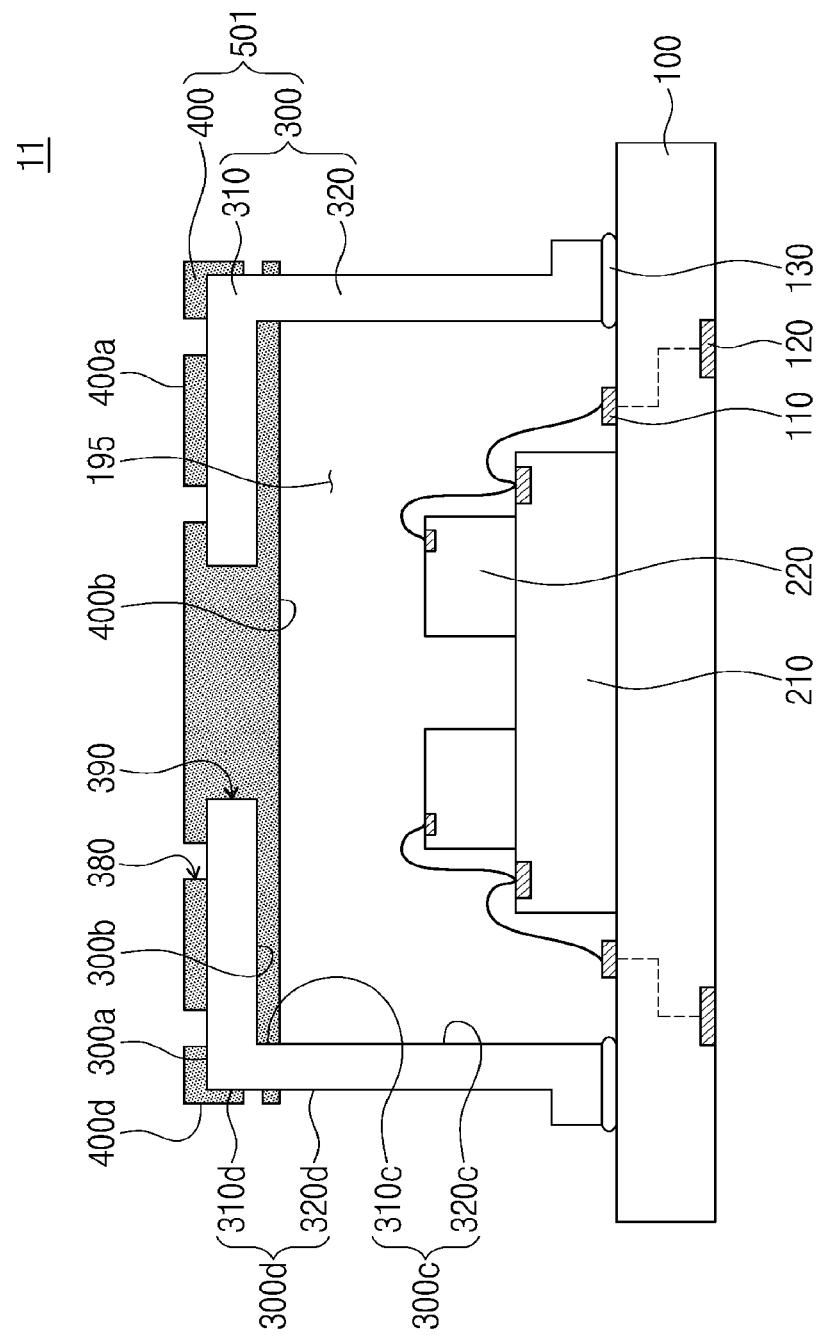

Referring to FIG. 3C, the waterproof film 400 may be separated from the container 600, with the result that a lid structure 501 may be fabricated. The lid structure 501 may include the lid 300 and the waterproof film 400. A first outer surface 300a of the lid 300 may be partially exposed to the recesses 380. A first sub-outer surface 310d of the lid 300 may be partially exposed to the recesses 380.

Referring back to FIG. 3D, a package substrate 100 may be prepared to have devices 210 and 220 mounted thereon. The lid structure 501 may be disposed on the package substrate 100, which step may manufacture a sensor package 11.

FIGS. 4A to 4D and 4F illustrate cross-sectional views showing a method of manufacturing a sensor package according to exemplary embodiments. In the embodiment that follows, a description duplicate with the aforementioned will be hereinafter omitted.

Figure 4A:
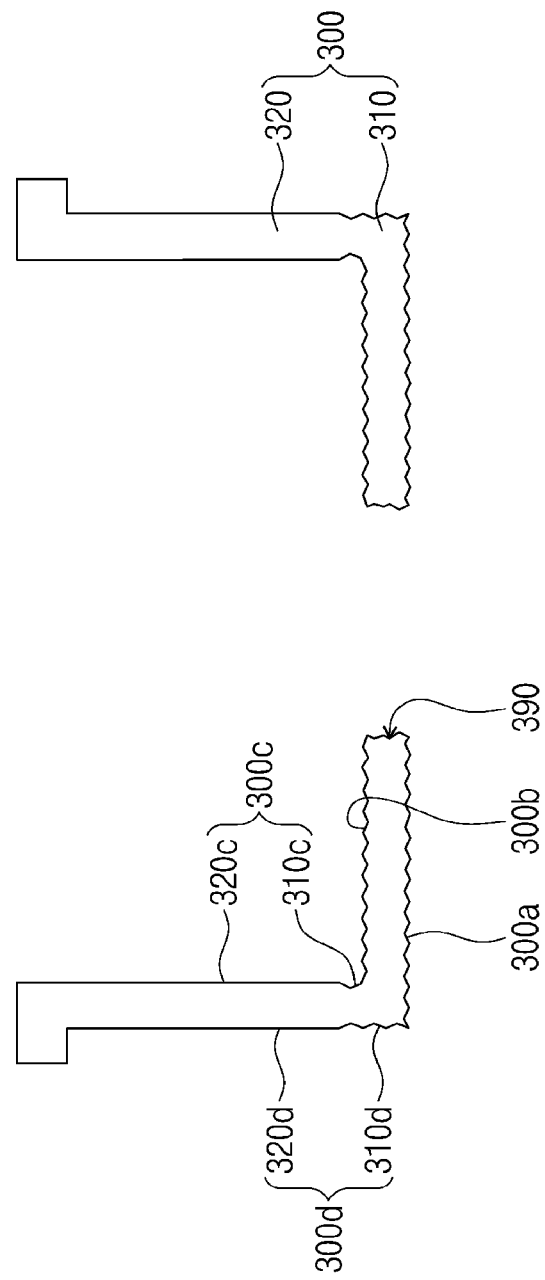
FIGS. 4A to 4D and 4F illustrate cross-sectional views showing a method of manufacturing a sensor package according to exemplary embodiments.

Referring to FIG. 4A, a surface treatment process may be performed on a first portion 310 of a lid 300. An etchant may be used to perform the surface treatment process on the lid 300. For example, the first portion 310 of the lid 300 may be provided in the etchant. The etchant may include an acid solution. For example, the acid solution may include sulfuric acid, nitric acid, hydrochloric acid, or a mixture thereof. For another example, a plasma treatment process may be used to perform the surface treatment process. The plasma treatment process may be an oxygen plasma treatment process. The surface treatment process may increase a surface roughness of the first portion 310 of the lid 300. The surface roughness of the first portion 310 of the lid 300 may fall within a range from about 30 nm to about 50 μm. According to exemplary embodiments, the surface roughness of the first portion 310 of the lid 300 may fall within a range from about 30 nm to about 50 tan as an arithmetic mean roughness (Ra). A second portion 320 of the lid 300 may not be exposed to the etchant. The surface roughness of the first portion 310 of the lid 300 may be greater than a surface roughness of the second portion 320 of the lid 300. The surface roughness of the first portion 310 of the lid 300 may indicate a surface roughness of one or more of a first sub-inner surface 310c of the lid 300, a first inner surface 300b of the lid 300, an inner wall of a hole 390 of the lid 300, a first outer surface 300a of the lid 300, and a first sub-outer surface 310d of the lid 300. The surface roughness of the second portion 320 of the lid 300 may indicate a surface roughness of a second sub-inner surface 320c of the lid 300 and a second sub-outer surface 320d of the lid 300.

Figure 4B:
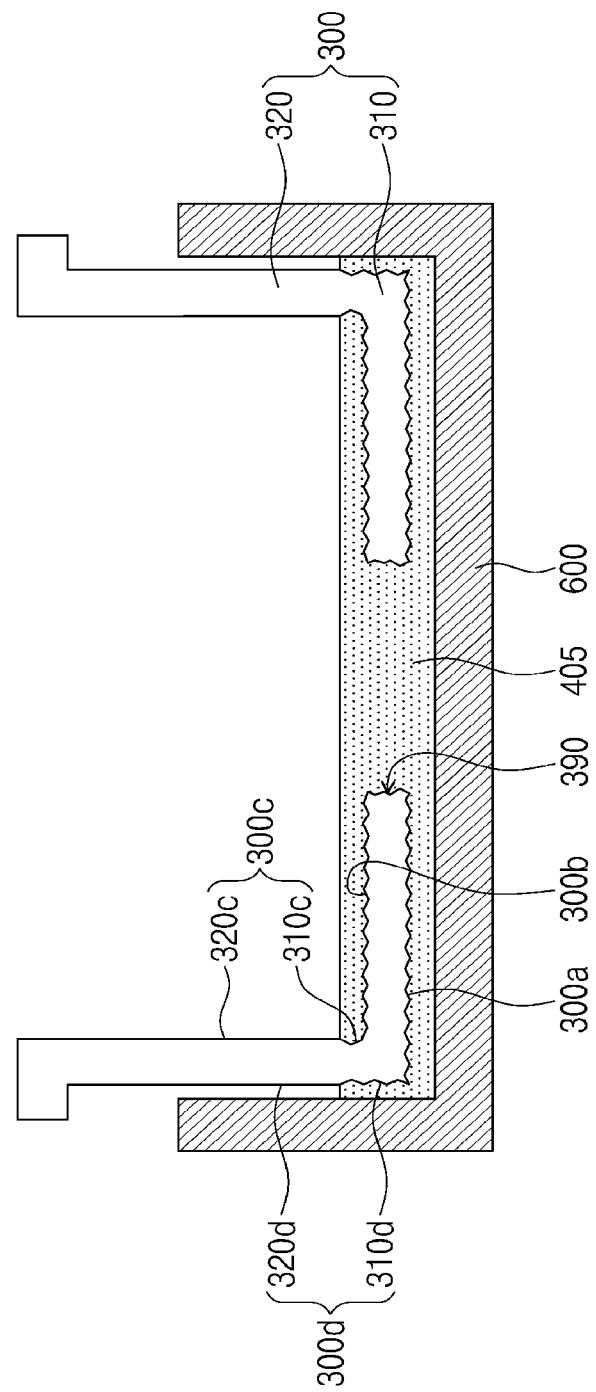

Referring to FIG. 4B, the first portion 310 of the lid 300 may be provided in a waterproof solution 405. The providing of the waterproof solution 405 may be substantially the same as that discussed with reference to FIG. 2B.

Figure 4C:
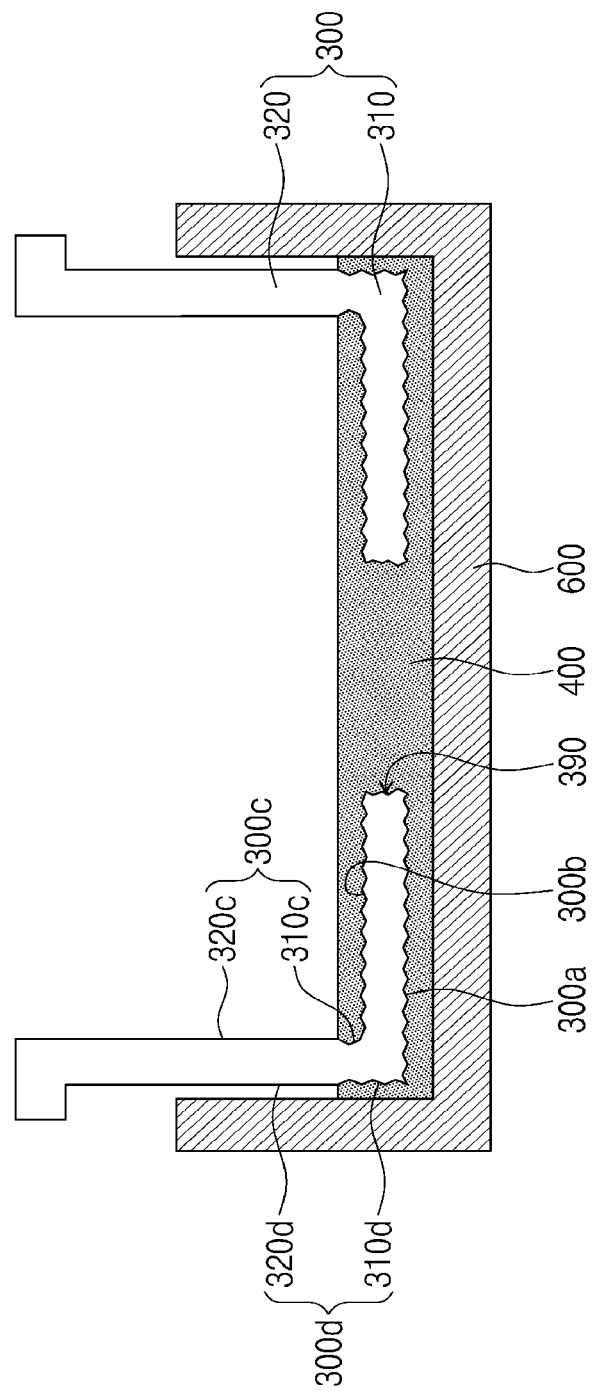
Figure 4D:
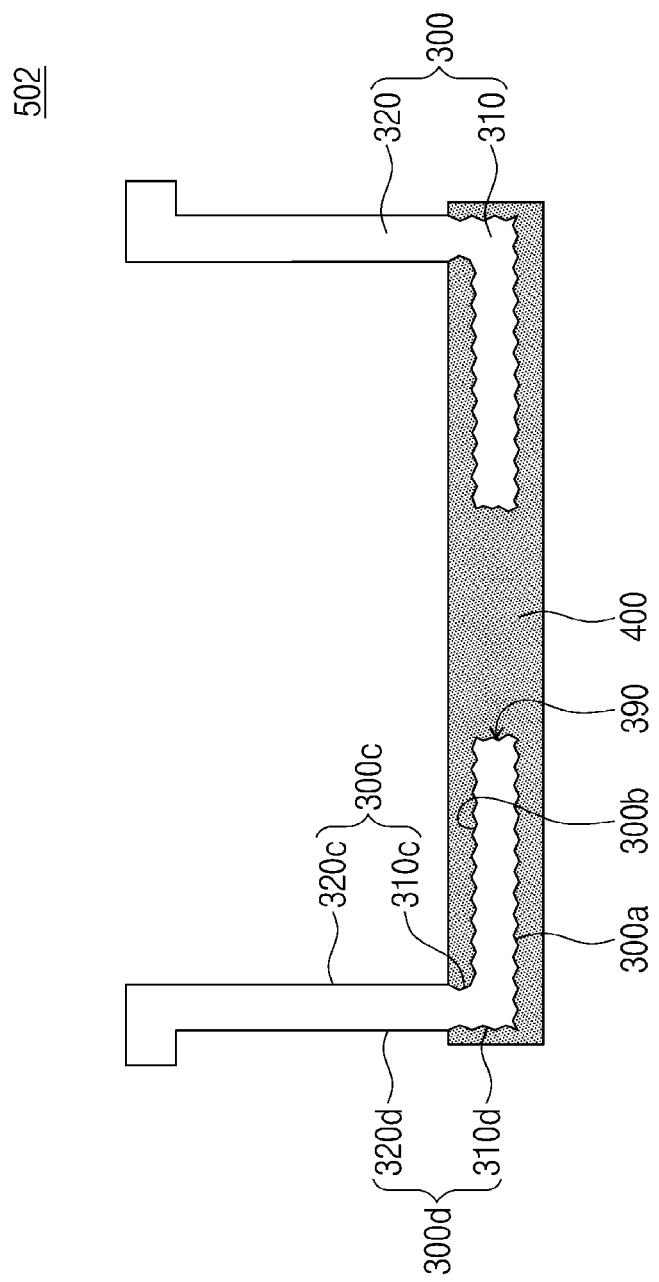

Referring successively to FIGS. 4C and 4D, the waterproof solution 405 may be cured to form a waterproof film 400. The waterproof film 400 may be formed on the first portion 310 of the lid 300. Since the first portion 310 of the lid 300 has a great surface roughness, an increased adhesive force may be provided between the lid 300 and the waterproof film 400. For example, an adhesive force may be greater between the lid 300 and the waterproof film 400 than between the waterproof film 400 and the container 600. Due to the difference in adhesive force, the waterproof film 400 may be easily separated from the container 600. A lid structure 502 may therefore be manufactured to include the lid 300 and the waterproof film 400.

Figure 4E:
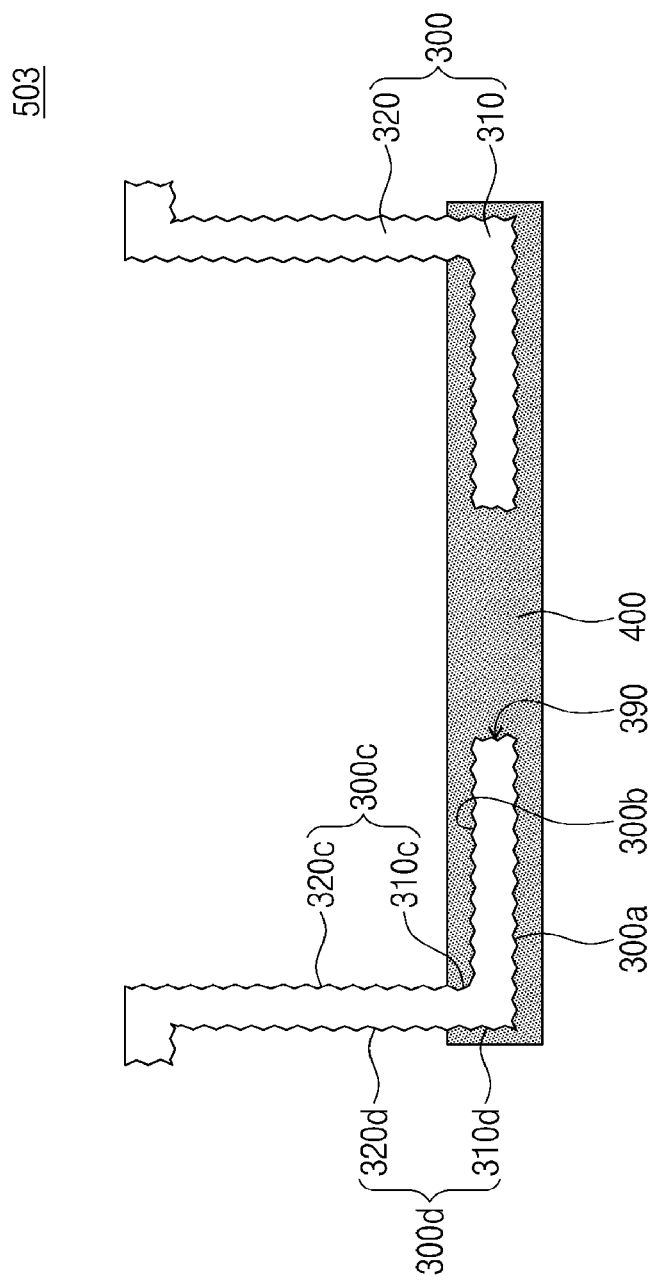
FIG. 4E illustrates a cross-sectional view showing a lid structure according to exemplary embodiments.
Figure 4F:
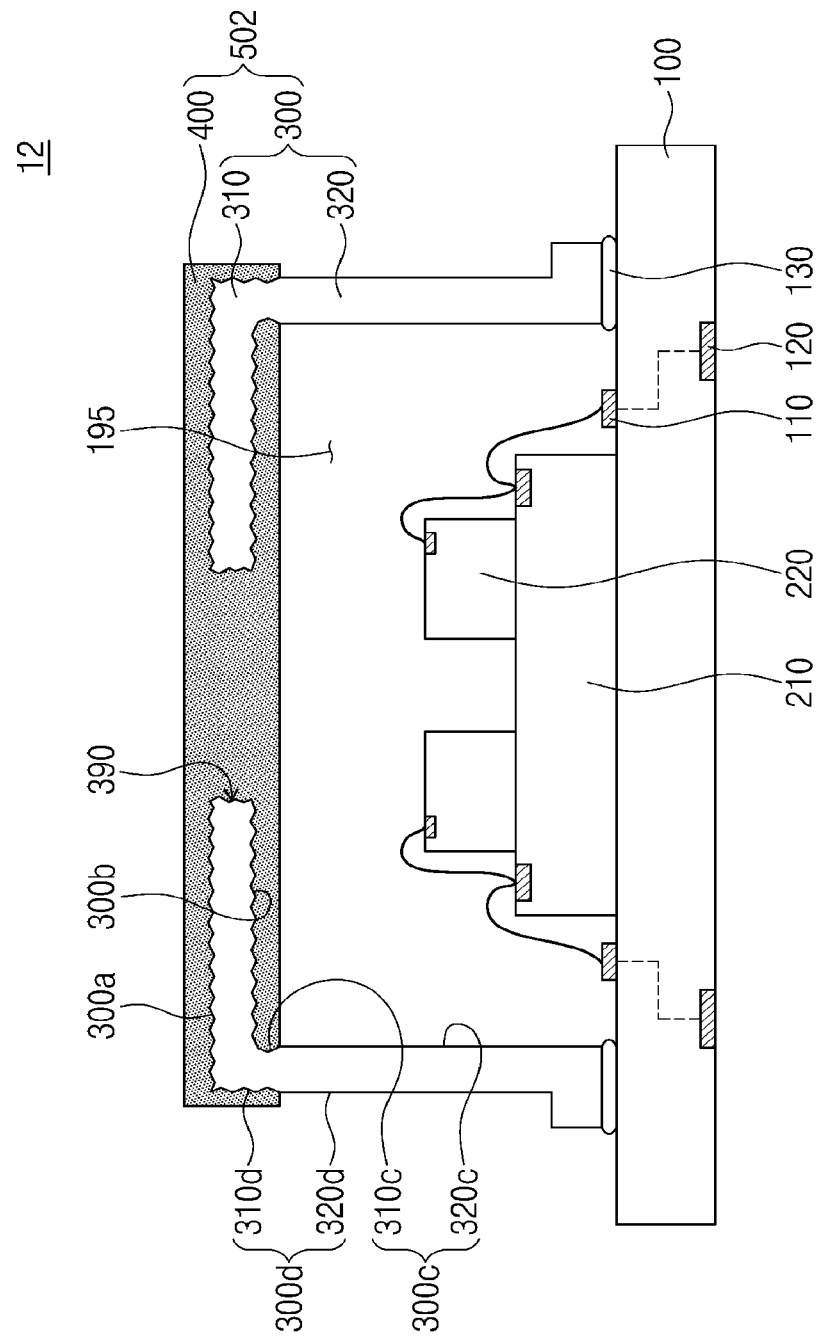

FIG. 4E illustrates a cross-sectional view showing a lid structure according to exemplary embodiments.

Referring to FIG. 4E, a lid structure 503 may include the lid 300 and the waterproof film 400. A surface treatment process may be performed on the lid 300 in manufacturing the lid structure 503. The surface treatment process may be performed identically or similarly to that discussed above with reference to FIG. 4A. The surface treatment process may be performed on the first and second portions 310 and 320 of the lid 300. The first and second portions 310 and 320 of the lid 300 may then have an increased surface roughness. For example, the surface roughness of the first and second portions 310 and 320 of the lid 300 may fall within a range from about 30 nm to about 50 μm. The waterproof film 400 may be formed in the hole 390 and on the first portion 310 of the lid 300. Since the lid 300 has a great surface roughness, the waterproof film 400 may be easily separated from the container 600 in fabricating the waterproof film 400.

Referring back to FIG. 4F, devices 210 and 220 may be mounted on a package substrate 100. The lid structure 502 may be disposed on the package substrate 100. The fabrication of the lid structure 502 may be identical or similar to that discussed with reference to FIGS. 4A to 4D. For another example, the lid structure 503 of FIG. 4E may be employed. Through the aforementioned exemplary processes, a sensor package 12 may be eventually manufactured.

FIGS. 5A to 5D illustrate cross-sectional views showing a method of manufacturing a sensor package according to exemplary embodiments. In the embodiment that follows, a description duplicate with the aforementioned will be omitted.

Figure 5A:
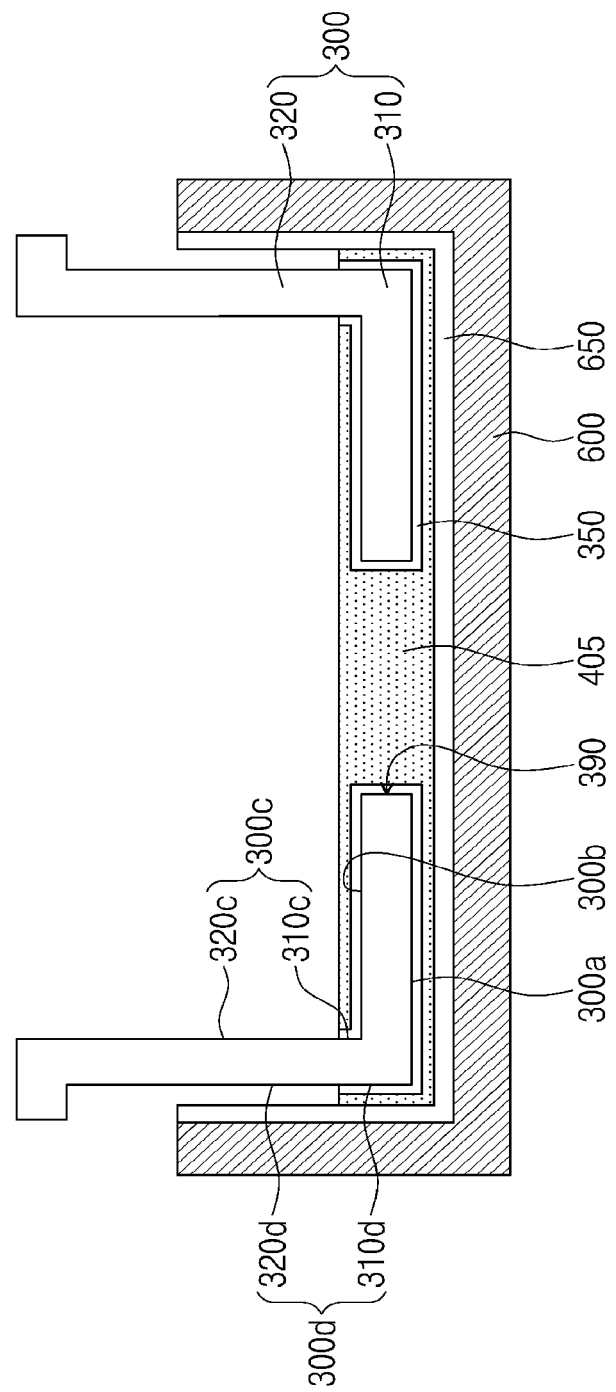
FIGS. 5A to 5D illustrate cross-sectional views showing a method of manufacturing a sensor package according to exemplary embodiments.

Referring to FIG. 5A, a container 600 may be prepared to have a separation assist film 650. The separation assist film 650 may be provided on an inner surface of the container 600. For example, the container 600 may include a metal, and the separation assist film 650 may include a polymer such as polyimide. A waterproof solution 405 may be provided on the separation assist film 650.

A lid 300 may be prepared to have an adhesion film 350 coated thereon. The adhesion film 350 may be formed on a first portion 310 of the lid 300 to cover an inner wall of a hole 390, a first outer surface 300a of the lid 300, a first inner surface 300b of the lid 300, and a first sub-inner surface 310c of the lid 300. The adhesion film 350 may further cover a first sub-outer surface 310d of the lid 300. The adhesion film 350 may not be formed on a second portion 320 of the lid 300. The adhesion film 350 may include a polymer.

The lid 300 may be provided in the waterproof solution 405. The waterproof solution 405 may fill the hole 390 and a gap between the separation assist film 650 and the adhesion film 350. Before the lid 300 is provided in the waterproof solution 405, a surface treatment process may further be performed as discussed with reference to FIG. 4A or 4D.

Figure 5B:
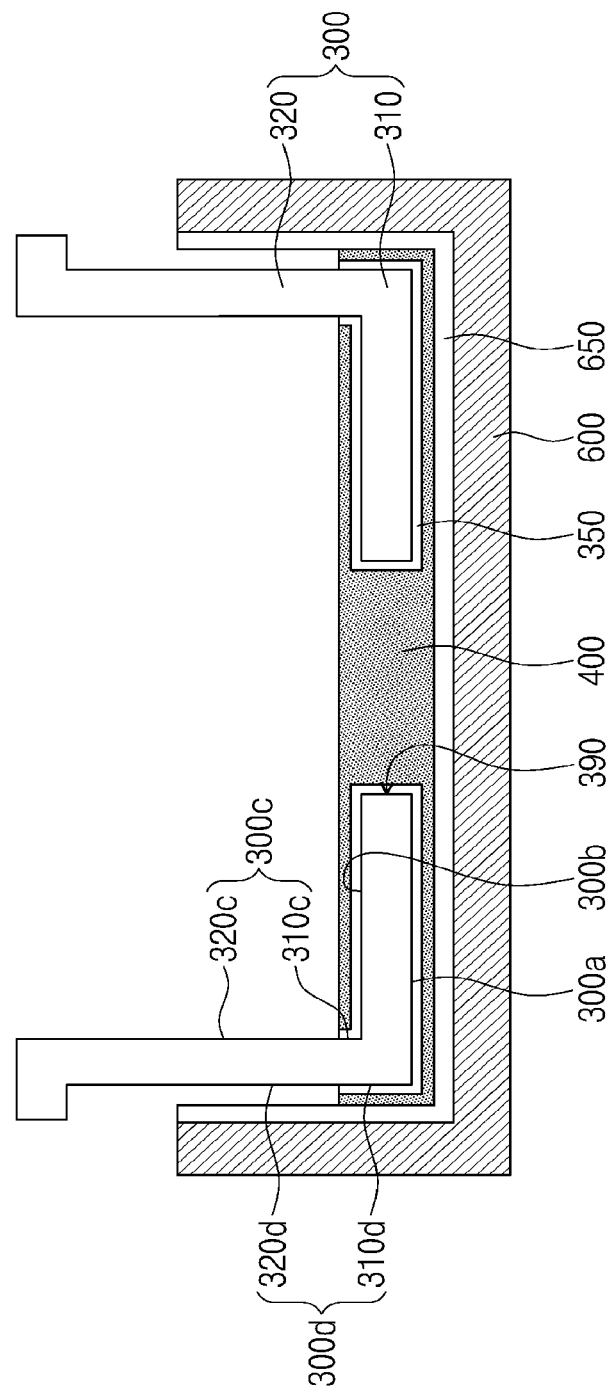
Figure 5C:
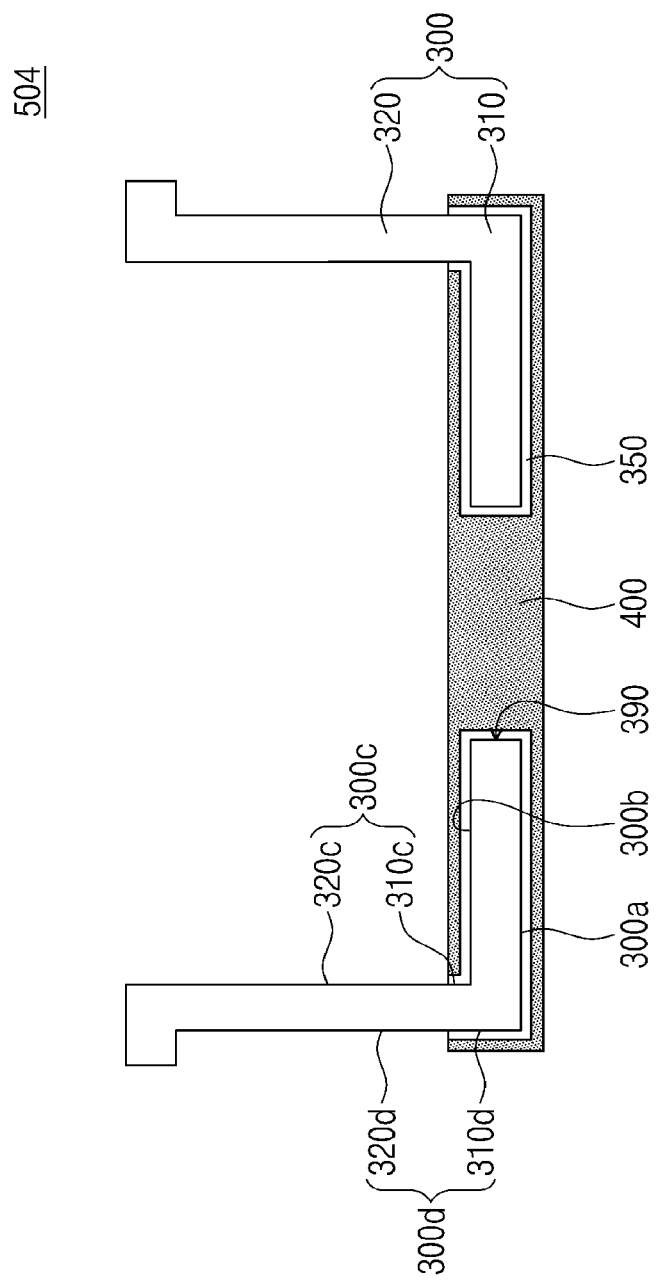
Figure 5D:
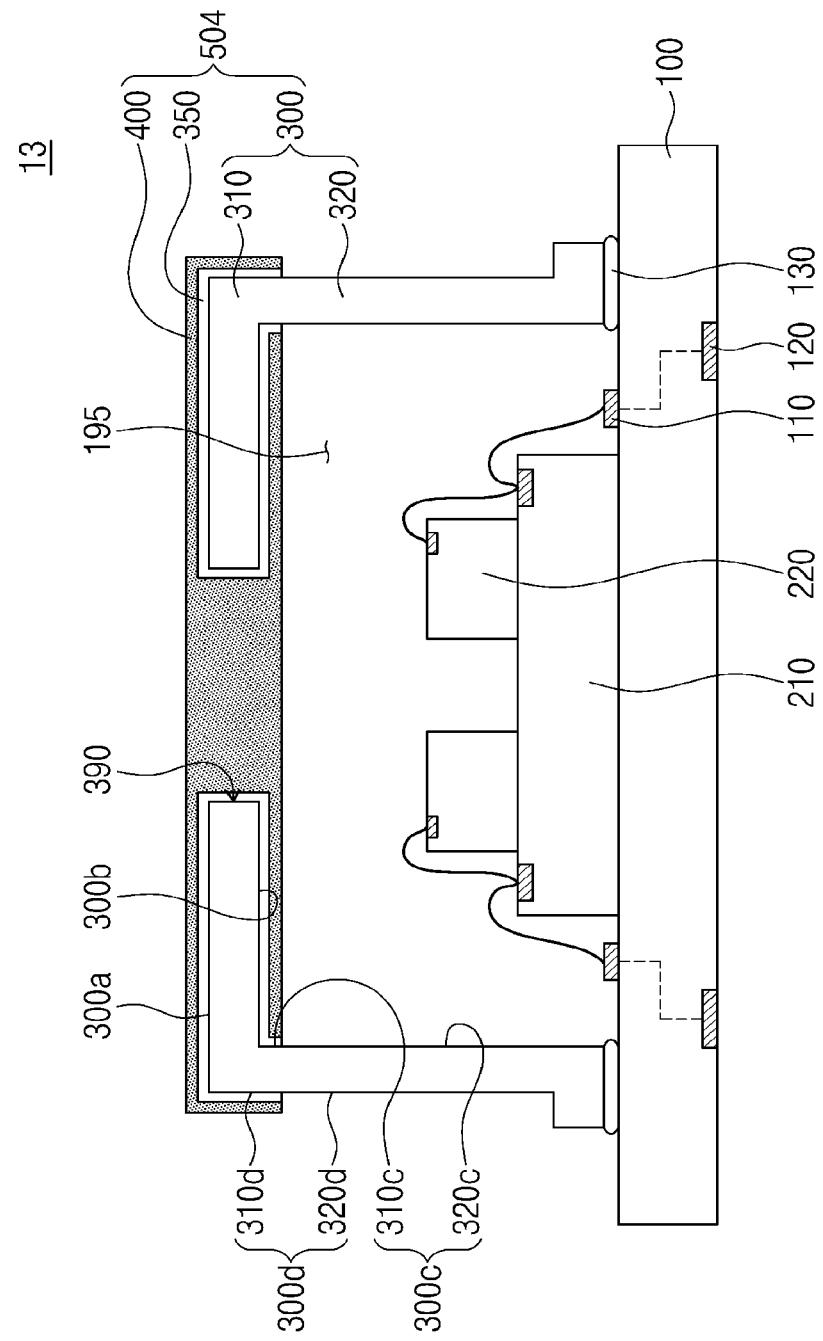

Referring successively to FIGS. 5B and 5C, the waterproof solution 405 may be cured to form a waterproof film 400. An increased adhesive force may be provided between the separation assist film 650 and the container 600. For example, an adhesive force may be greater between the separation assist film 650 and the container 600 than between the separation assist film 650 and the adhesion film 350. In some embodiments, the adhesion film 350 may not be provided, and in this case, an adhesive force may be greater between the separation assist film 650 and the container 600 than between the separation assist film 650 and the waterproof film 400. The separation assist film 650 may easily separate the waterproof film 400 from the container 600. As illustrated in FIG. 5C, a lid structure 504 may include the adhesion film 350 in addition to the lid 300 and the waterproof film 400. The adhesion film 350 may be interposed between the lid 300 and the waterproof film 400. The adhesion film 350 may more rigidly adhere the waterproof film 400 onto the lid 300.

Referring back to FIG. 5D, devices 210 and 220 may be mounted on a package substrate 100. The lid structure 504 may be disposed on the package substrate 100, which step may manufacture a sensor package 13.

Figure 6:
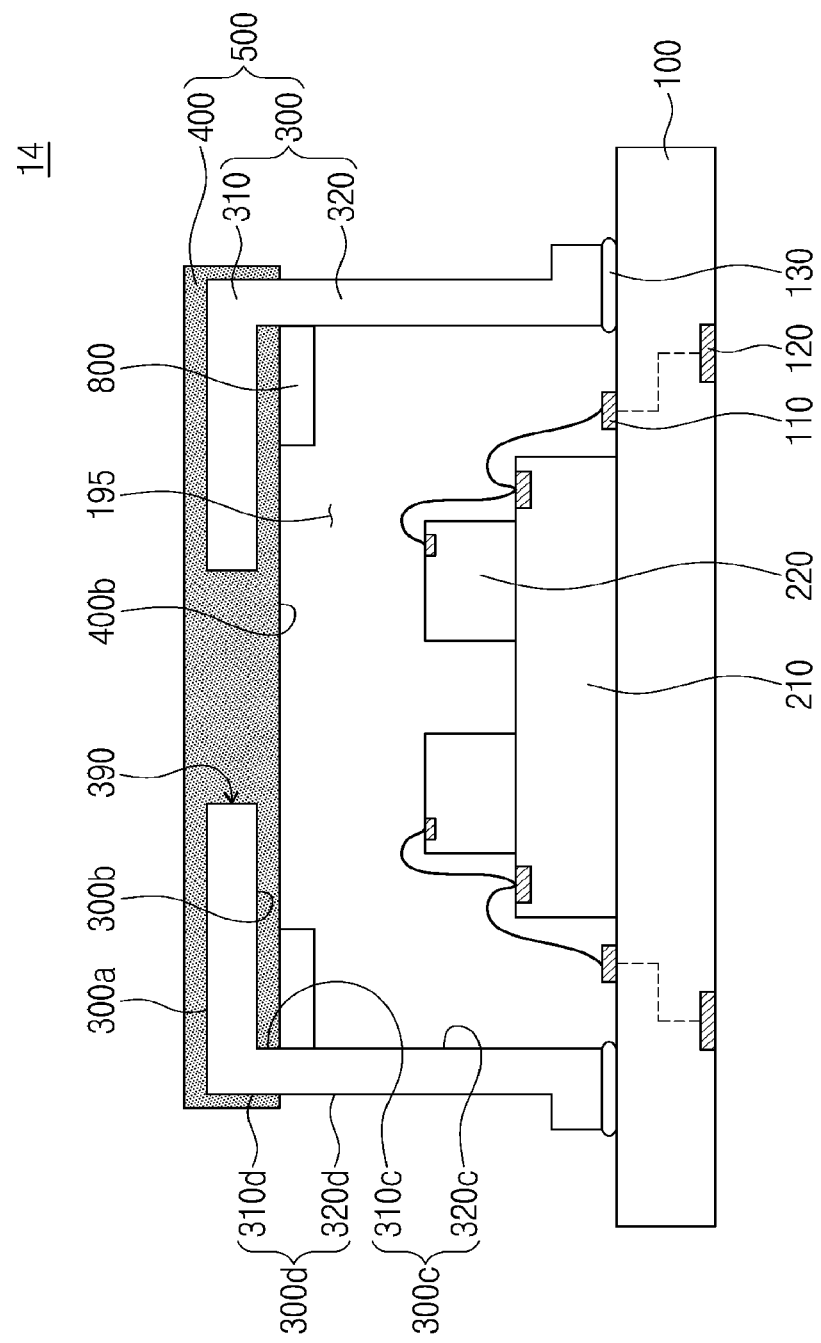

FIG. 6 illustrates a plan view showing a sensor package according to exemplary embodiments. In the embodiment that follows, a description duplicate with the aforementioned will be omitted.

Referring to FIG. 6, a sensor package 14 may include a package substrate 100, a control device 210, a sensing device 220, a lid structure 500, and an adhesion portion 800. The package substrate 100, the control device 210, the sensing device 220, and the lid structure 500 may be the same as those discussed above with reference to FIG. 1. For example, the lid structure 500 may be substantially the same as the lid structure 500 of FIG. 1. For another example, the sensor package 14 may include one of the lid structure 501 of FIG. 3C, the lid structure 502 of FIG. 4D, the lid structure 503 of FIG. 4E, and the lid structure 504 of FIG. 5C. A bottom surface 400b of the waterproof film 400 may face the package substrate 100.

The adhesion portion 800 may be disposed on the bottom surface 400b of the waterproof film 400. The adhesion portion 800 may be in physical contact with the bottom surface 400b of the waterproof film 400 and a second inner surface 300c of the lid 300. The adhesion portion 800 may more rigidly fix the waterproof film 400 to the lid 300. In some embodiments, the adhesion portion 800 may be formed after the waterproof film 400 is formed. The formation of the adhesion portion 800 may be performed before or after the waterproof film 400 is separated from the container 600.

According to inventive concepts, the waterproof film may prevent impurities from entering the hole. It therefore may be possible to prevent or reduce damages to the sensing device and the occurrence of sensing noise due to the impurities.

In some embodiments, the formation of the waterproof film may include providing the lid structure in the waterproof solution and curing the waterproof solution. The waterproof film may thus be formed in a simplified process. The waterproof film may be formed in a hole of the lid without a limitation of a size of the hole of the lid.

This detailed description of inventive concepts should not be construed as limited to the embodiments set forth herein, and it is intended that inventive concepts cover the various combinations, the modifications and variations of this invention without departing from the spirit and scope of inventive concepts. The appended claims should be construed to include other embodiments.

What is claimed is:

1. A method of manufacturing a lid structure, the method comprising:
preparing a lid including a first portion and a second portion, the first portion of lid has a hole extending between a first inner surface and an first outer surface of the lid;
filling the hole with a waterproof solution by placing the first portion of the lid into the waterproof solution; and
curing the waterproof solution to form a waterproof film in the hole,
wherein the waterproof film is formed in the hole and on the first inner surface and the first outer surface of the lid,
wherein the lid has the first inner surface, the first outer surface, a second outer surface, and an outer edge, the outer edge provided at a location where the first outer surface meets the second outer surface, and
wherein the second outer surface of the lid corresponds to an outer sidewall of the lid.

2. The method of claim 1, wherein the second portion of the lid is not immersed in the waterproof solution during the placing the first portion of the lid into the waterproof solution.

3. The method of claim 2, wherein the second outer surface of the lid comprises a first sub-outer surface and a second sub-outer surface,
wherein the first sub-outer surface is provided between the second sub-outer surface and the outer edge of the lid, and
wherein the placing the first portion of the lid into the waterproof solution comprises immersing the first sub-outer surface of the lid in the waterproof solution without immersing the second sub-outer surface of the lid.

4. The method of claim 3, further comprising:
performing a surface treatment process on the first portion of the lid to increase a surface roughness of the first portion of the lid,
wherein the second portion of the lid is not exposed to the surface treatment process.

5. The method of claim 1, wherein preparing the lid structure further comprises:
adding the waterproof solution to a container, the container having protrusion on an inner surface thereof; and
placing the lid on the protrusion to cause the lid to come into contact with the protrusion.

6. The method of claim 5, further comprising:
separating the waterproof film from the container,
after the separating the waterproof film from the container, the waterproof film having a recess on a top surface thereof, the recess corresponding to the protrusion of the container.

7. The method of claim 1, wherein the waterproof film comprises a hydrophobic polymer.

8. The method of claim 1, wherein the preparing the lid further comprises providing an adhesion film on the first portion of the lid,
wherein the adhesion film is provided between the lid and the waterproof film, after the curing the waterproof solution.

9. The method of claim 8, further comprising:
preparing a container and a separation assist film, the separation assist film provided on an inner surface of container; and
adding the waterproof solution on the separation assist film in the container,
wherein after the curing the waterproof solution, an adhesive force between the separation assist film and the container is greater than an adhesive force between the separation assist film and the waterproof film.

10. A method of manufacturing a lid structure, the method comprising:
preparing a lid, the lid having:
a first inner surface;
a first outer surface opposite to the first inner surface;
a second inner surface corresponding an inner sidewall of the lid;
a second outer surface opposite to the second inner surface, the second outer surface including a first sub-outer surface and a second sub-outer surface;
an outer edge provided at a location where the first outer surface meets the second outer surface, the first sub-outer surface provided between the outer edge and the second sub-outer surface; and a hole extending between the first inner surface and the first outer surface; and filling the hole with a waterproof solution by placing a portion of the lid into the waterproof solution; and curing the waterproof solution to form a waterproof film in the hole, wherein the waterproof film is formed in the hole and provided on the first inner surface, the first outer surface, the outer edge, and the first sub-outer surface of the lid, wherein the second sub-outer surface is exposed by the waterproof film, wherein the waterproof film comprises a hydrophobic polymer, and wherein the waterproof film has pores, each of the pores having a diameter ranging from 0.1 μm to 10 μm.

11. A method of manufacturing a sensor package, the method comprising:

preparing a lid structure; and placing the lid structure on a package substrate, wherein the lid structure comprises:

a lid having a hole extending between a first inner surface and a first outer surface of the lid, the first inner surface of the lid facing toward the package substrate and the first outer surface of the lid facing away from the package substrate; and a waterproof film in the hole and on the first inner surface and the first outer surface of the lid.

12. The method of claim 11, where the lid comprises:

a first portion covered by the waterproof film and having the first inner surface and the first outer surface; and a second portion exposed by the waterproof film, wherein the second portion of the lid is provided between the first portion of the lid and the package substrate.

13. The method of claim 11, wherein the lid further has a second outer surface and an outer edge, the outer edge provided at a location that the first outer surface meets the second outer surface, wherein the second outer surface of the lid comprises a first sub-outer surface and a second sub-outer surface, wherein the first sub-outer surface is provided between the second sub-outer surface and the outer edge of the lid, and, wherein the waterproof film covers the first sub-outer surface and exposes the second sub-outer surface of the lid.

14. The method of claim 13, wherein the first sub-outer surface of the lid has a surface roughness greater than a surface roughness of the second sub-outer surface of the lid.

15. The method of claim 14, the surface roughness of the first sub-outer surface of the lid falls within a range from about 30 nm to about 50 μm.

16. The method of claim 11, wherein the waterproof film has a recess on a surface thereof, and wherein the recess exposes the first outer surface of the lid.

17. The method of claim 11, wherein the lid structure further comprises an adhesion film between the lid and the waterproof film.

18. The method of claim 11, further comprising:

mounting a control device on the package substrate; and mounting gas sensors on the control device.

19. The method of claim 11, wherein the waterproof film has pores, each of the pores having a diameter ranging from 0.1 μm to 10 μm, and wherein the waterproof film has a thickness ranging from 10 μm to 500 μm in the hole.

20. The method of claim 11, wherein the waterproof film comprises poly(tetrafluoroethylene).

* * * * *